United States Patent
Verma et al.

(10) Patent No.: US 10,766,836 B2
(45) Date of Patent: Sep. 8, 2020

(54) METHODS AND SYSTEMS FOR SEPARATING OLEFINS

(71) Applicant: Kellogg Brown & Root LLC, Houston, TX (US)

(72) Inventors: Vijender Kumar Verma, Sugar Land, TX (US); Curtis Eng, Sugar Land, TX (US)

(73) Assignee: KELLOGG BROWN & ROOT LLC, Houston, TX (US)

( * ) Notice: Subject to any disclaimer, the term of this patent is extended or adjusted under 35 U.S.C. 154(b) by 0 days.

(21) Appl. No.: 14/210,035

(22) Filed: Mar. 13, 2014

(65) Prior Publication Data

US 2014/0275674 A1 Sep. 18, 2014

Related U.S. Application Data

(60) Provisional application No. 61/783,970, filed on Mar. 14, 2013.

(51) Int. Cl.
| | |
|---|---|
| *C07C 7/167* | (2006.01) |
| *C07C 7/09* | (2006.01) |
| *C10G 7/00* | (2006.01) |
| *C10G 45/32* | (2006.01) |
| *F25J 3/02* | (2006.01) |

(52) U.S. Cl.
CPC ............... *C07C 7/167* (2013.01); *C07C 7/09* (2013.01); *C10G 7/00* (2013.01); *C10G 45/32* (2013.01); *F25J 3/0219* (2013.01); *F25J 3/0233* (2013.01); *F25J 3/0238* (2013.01); *F25J 3/0242* (2013.01); *F25J 3/0252* (2013.01); *C10G 2300/1088* (2013.01); *C10G 2400/20* (2013.01); *F25J 2205/04* (2013.01); *F25J 2210/04* (2013.01); *F25J 2210/12* (2013.01); *F25J 2215/62* (2013.01); *F25J 2230/30* (2013.01); *F25J 2245/02* (2013.01); *Y02P 30/40* (2015.11); *Y02P 30/462* (2015.11)

(58) Field of Classification Search
CPC ................ C07C 5/08; C07C 7/00; C07C 7/04
USPC .......................................................... 585/259
See application file for complete search history.

(56) References Cited

U.S. PATENT DOCUMENTS

| | | | | |
|---|---|---|---|---|
| 2,629,753 | A * | 2/1953 | Frevel ................... | C07C 5/3335 585/634 |
| 2,736,756 | A * | 2/1956 | Elgin ........................ | C07C 7/11 585/835 |

(Continued)

*Primary Examiner* — Youngsul Jeong
(74) *Attorney, Agent, or Firm* — Gary M. Machetta (57) ABSTRACT

Systems and methods for separating one or more olefins are provided. In one or more embodiments, the method for separating one or more olefins can include separating at least a portion of one or more $C_3$ and heavier hydrocarbons from a hydrocarbon containing $C_1$ to $C_{20}$ hydrocarbons to provide a first mixture that can include methane, ethane, ethylene, and/or acetylene. At least a portion of the first mixture can be hydrogenated to convert at least a portion of the acetylene to ethane and ethylene. At least a portion of the methane can be separated from the hydrogenated mixture to provide a second mixture that can include ethane and ethylene. At least a portion of the ethylene can be separated from the second mixture to provide a first product that can include at least 95 mol % ethylene and a second product that can include at least 95 mol % ethane.

19 Claims, 2 Drawing Sheets

(56) References Cited

U.S. PATENT DOCUMENTS 5,689,032 A * 11/1997 Krause ................... C07C 7/005
                                                      208/100
6,578,378 B2 * 6/2003 Kaiser .................. C10G 70/043
                                                       62/622

* cited by examiner

METHODS AND SYSTEMS FOR SEPARATING OLEFINS

CROSS-REFERENCE TO RELATED APPLICATION

This application claims priority to U.S. Provisional Patent Application having Ser. No. 61/783,970, filed Mar. 14, 2013, which is incorporated by reference herein.

BACKGROUND

Field

Embodiments described generally relate to systems and methods for separating olefinic hydrocarbons.

Description of the Related Art

Olefins are typically produced by converting a hydrocarbon feed at a high temperature to provide a hydrocarbon mixture containing various alkane, alkene, and alkyne hydrocarbons. The hydrocarbon mixture is then fractionated using a series of distillation columns, fractionation columns, compressors, and refrigeration systems to cool, condense, and separate the various hydrocarbon products. Due to the relatively low boiling points of low molecular weight hydrocarbons, ethylene and propylene are frequently employed as refrigerants while separating and fractionating the hydrocarbon mixture.

Many olefin production processes provide a hydrocarbon mixture rich in $C_2$-$C_4$ alkanes and alkenes. The $C_3$ and $C_4$ hydrocarbons can be separated from the hydrocarbon mixture, in part, due to the higher boiling points of $C_3$ and $C_4$ hydrocarbons relative to other compounds in the hydrocarbon mixture. However, the separation of the $C_2$ hydrocarbons into relatively pure (e.g., greater than 95 mol %) ethane and ethylene products requires the use of very low temperature (e.g., about −50° C. to about −140° C.) vapor-liquid flash and fractional distillation processes due to the relatively similar boiling points of ethylene (e.g., about −103.7° C.) and ethane (e.g., about −88.6° C.). Two or more refrigeration systems employing low temperature propylene and ethylene refrigerants are required to separate the methane, hydrogen, and ethylene from ethane. The need for dual refrigerant, low temperature, refrigeration systems requires both significant capital costs and significant operating costs. Further, the low operating temperatures and high operating pressures require the use of special metallurgies and equipment construction imposing additional capital and operating costs.

There is a need, therefore, for improved methods and systems for separating ethane and/or ethylene from a hydrocarbon mixture that in addition to ethane and/or ethylene also includes one or more additional $C_1$ to $C_{20}$ hydrocarbons.

DETAILED DESCRIPTION

Methods and system for separating one or more olefins are provided. In one or more embodiments, the method for separating one or more olefins can include separating at least a portion of one or more $C_3$ and heavier hydrocarbons from a hydrocarbon containing $C_1$ to $C_{20}$ hydrocarbons to provide a first hydrocarbon mixture that can include one or more of methane, ethane, ethylene, and/or acetylene (ethyne). At least a portion of the first hydrocarbon mixture can be hydrogenated to convert at least a portion of the acetylene to ethane and ethylene. At least a portion of the methane can be separated from the hydrogenated mixture to provide a second hydrocarbon mixture that can include ethane and ethylene. At least a portion of the ethylene can be separated from the second hydrocarbon mixture to provide a first product that can include at least 95 mol % ethylene and a second product that can include at least 95 mol % ethane. The ethylene can be separated from the second hydrocarbon mixture at a pressure of about 360 kPa to about 4,000 kPa or about 500 kPa to about 2,500 kPa.

Figure 1:
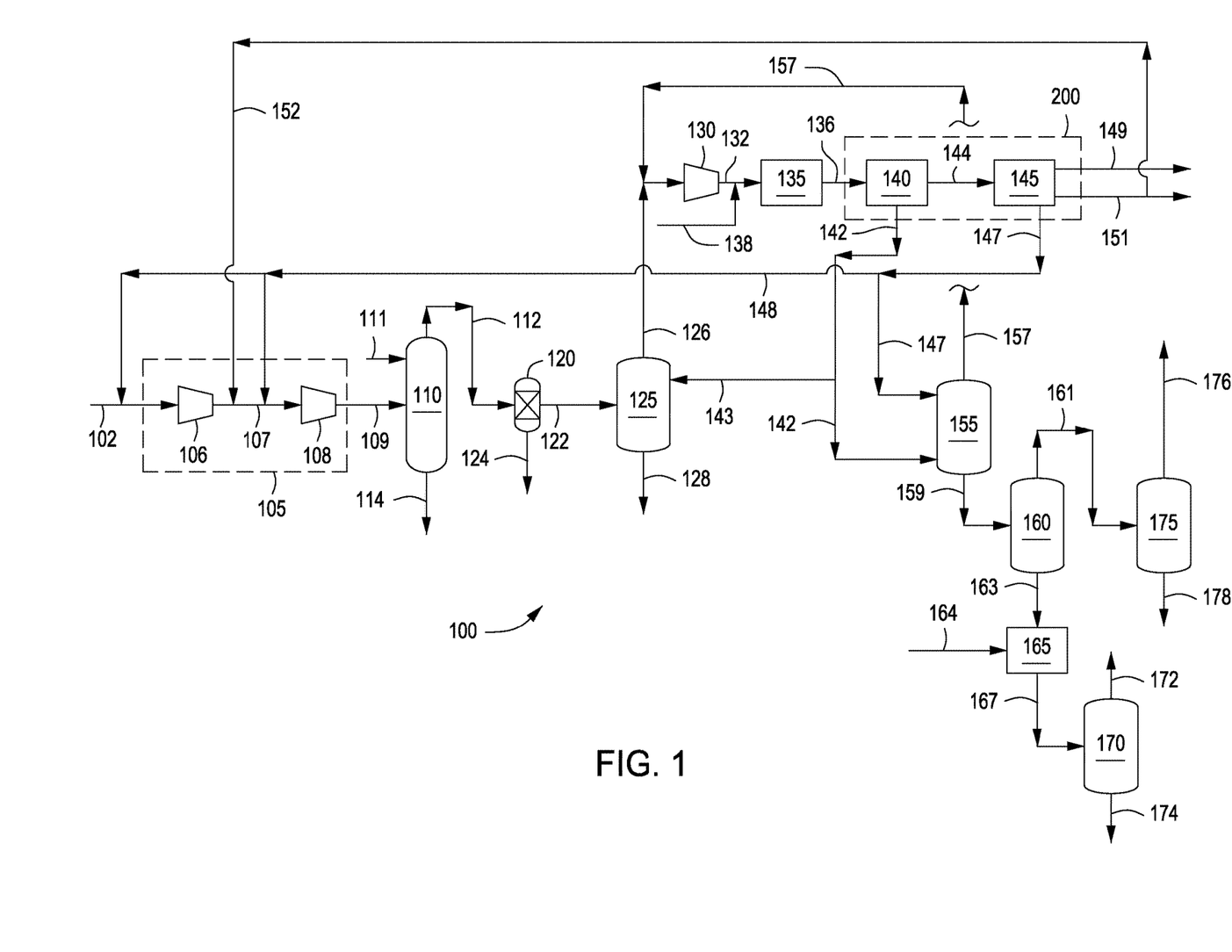
FIG. 1 depicts an illustrative system for separating hydrocarbons, according to one or more embodiments described.

FIG. 1 depicts an illustrative system 100 for separating hydrocarbons according to one or more embodiments. The system 100 can include one or more compressors (two are shown 105, 130), one or more scrubbers 110, one or more driers 120, one or more vapor-liquid separators (five are shown 125, 155, 160, 170, 175), one or more reactor systems (two are shown 135, 165), and one or more chilling systems 200. The chilling system 200 can include one or more coolers or cooling systems (two are shown 140, 145). One or more hydrocarbons via line 102 can be introduced to the compressor 105 to provide a compressed fluid (e.g., compressed hydrocarbon fluid having gaseous and/or liquid state) via line 109. The hydrocarbon in line 102 can include one or more liquid hydrocarbons, gaseous hydrocarbons, fluidized hydrocarbons, or any mixture thereof. The hydrocarbon in line 102 can include, but is not limited to, one or more $C_1$ to $C_{20}$ hydrocarbons. The $C_1$ to $C_{20}$ hydrocarbons can include, but are not limited to, one or more alkanes, one or more alkenes, one or more alkynes, or any mixture thereof. The hydrocarbon in line 102 can also include one or more acid gases. Illustrative acid gases can include, but are not limited to, carbon dioxide and/or hydrogen sulfide. The hydrocarbon in line 102 can also include one or more sour gases or compounds. Illustrative sour gases or compounds can include, but are not limited to, hydrogen sulfide and organosulfur compounds, such as mercaptans. The hydrocarbon in line 102 can include, but is not limited to, hydrogen, methane, ethane, ethylene, acetylene, propane, propylene, butane, butane, pentane, pentene, isomers thereof, or any mixture thereof.

The hydrocarbon in line 102 can include hydrogen in an amount of about 0.5 mol %, about 1 mol %, about 2 mol %, about 3 mol %, about 4 mol %, or less than 5 mol % to 5 mol %, less than 10 mol %, less than 15 mol %, or less than 25 mol %. The methane concentration in the hydrocarbon in line 102 can be about 0.5 mol %, about 1 mol %, about 2 mol %, about 3 mol %, about 4 mol %, or less than 5 mol % to 5 mol %, less than 10 mol %, less than 15 mol %, or less than 25 mol %. The ethane concentration in the hydrocarbon in line 102 can be about 0.5 mol %, about 1 mol %, about 2 mol %, about 3 mol %, about 4 mol %, or less than 5 mol % to 5 mol %, less than 10 mol %, less than 15 mol %, or less than 25 mol %. The ethylene concentration in the hydrocarbon in line 102 can be about 0.5 mol %, about 1 mol %, about 2 mol %, about 3 mol %, about 4 mol %, or less than 5 mol % to 5 mol %, less than 10 mol %, less than 15 mol %, or less than 25 mol %. The acetylene concentration in the hydrocarbon in line 102 can be about 0.1 mol %, about 0.5 mol %, about 0.75 mol %, about 1 mol %, or less than 2 mol % to 2 mol %, less than 3 mol %, less than 5 mol %, or less than 10 mol %. The propane concentration in the hydrocarbon in line 102 can be about 0.5 mol %, about 1 mol %, about 2 mol %, about 3 mol %, about 4 mol %, or less than 5 mol % to 5 mol %, less than 10 mol %, less than 15 mol %, or less than 25 mol %. The propylene concentration in the hydrocarbon in line 102 can be about 0.5 mol %, about 1 mol %, about 2 mol %, about 3 mol %, about 4 mol %, or less than 5 mol % to 5 mol %, less than 10 mol %, less than 15 mol %, or less than 25 mol %. The acid gas concentration in the hydrocarbon in line 102 can be about 0.01 mol %, about 0.05 mol %, about 0.1 mol %, about 0.2 mol %, about 0.3 mol %, about 0.4 mol %, or less than 0.5 mol % to 0.5 mol %, less than 0.7 mol %, less than 1 mol %, less than 1.3 mol %, or less than 1.5 mol %. The sour gas concentration in the hydrocarbon in line 102 can be about 0.01 mol %, about 0.05 mol %, about 0.1 mol %, about 0.2 mol %, about 0.3 mol %, about 0.4 mol %, or less than 0.5 mol % to 0.5 mol %, less than 0.7 mol %, less than 1 mol %, less than 1.3 mol %, or less than 1.5 mol %.

The hydrocarbon in line 102 can be at a pressure of about 100 kPa, about 300 kPa, about 500 kPa, or about 700 kPa to about 800 kPa, about 1,000 kPa, about 1,300 kPa, or about 1,500 kPa. The hydrocarbon in line 102 can be at a temperature of about 0° C., about 5° C., about 10° C., or about 15° C. to about 75° C., about 80° C., about 90° C., or about 100° C.

In one or more embodiments, one or more $C_4$ and heavier hydrocarbons (e.g., $C_4$+ hydrocarbons) can be cracked or otherwise processed in a high temperature, pyrolytic process to produce the hydrocarbon in line 102. In other embodiments, one or more $C_3$ and heavier hydrocarbons from a hydrocarbon containing $C_1$ to $C_{20}$ hydrocarbons can be separated or otherwise processed to produce the hydrocarbon in line 102. Illustrative pyrolytic processes can include, but are not limited to, fluid catalytic cracking ("FCC"), thermal cracking, hydrocracking, or any combination thereof. An illustrative advanced catalytic olefins ("ACO") process and system suitable for producing at least a portion of the hydrocarbon in line 102 can include those discussed and described in U.S. Pat. No. 7,301,063. An illustrative methanol to olefins ("MTO") process and system, suitable for producing at least a portion of the hydrocarbon in line 102 can include those discussed and described in U.S. Pat. Nos. 5,191,141; 4,590,320; 4,550,217; and 4,496,786. As such, at least a portion of the hydrocarbon in line 102 can be produced by cracking a heavy hydrocarbon containing $C_4$+ hydrocarbons in a fluid catalytic cracker, an advanced catalytic olefins process, a methanol to olefins process, a thermal cracker, a hydrocracker, or any combination thereof.

In one or more embodiments, the hydrocarbon in line 102 produced via one or more pyrolytic processes, such as the FCC, ACO, and/or MTO process, can have low concentrations of hydrogen and methane. For example, the hydrocarbon in line 102 can include less than 15 mol % hydrogen and less than 15 mol % methane. The low hydrogen and methane concentrations can permit the separation of the hydrogen and methane from the hydrocarbon at pressures greater than 1,000 kPa and temperatures greater than the boiling point of propylene (e.g., about −47.4° C.) to provide an ethylene/ethane mixture. The reduced concentration of hydrogen and methane in the ethane/ethylene mixture can permit subsequent separation of the ethylene/ethane mixture into a relatively pure ethane product, e.g., greater than 95 mol % ethane, and a relatively pure ethylene product, e.g., greater than 95 mol % ethylene, at a pressure of about 360 kPa or greater and a temperature of about −47.4° C. or greater. The power required to provide the higher separation pressure, however, increases the overall energy consumption.

As depicted in FIG. 1, the compressor 105 can include a first stage 106 that can provide a first compressed fluid (e.g., compressed hydrocarbon fluid having gaseous and/or liquid state) via line 107 and a second stage 108 that can provide the first compressed fluid via line 109. In one or more embodiments, the first stage 106 and the second stage 108 can be separate, independent compressors. The one or more compressors 105 can include one or more systems, devices or combination of systems and/or devices suitable for compressing a fluid at a first pressure to provide a fluid at a second pressure, where the second pressure is greater than the first pressure. In one or more embodiments, the pressure of the compressed fluid in line 102 can be increased by about 500 kPa or greater, about 1,000 kPa or greater, about 1,500 kPa or greater, or about 2,000 kPa or greater by passage through the first stage 106 and the second stage 107. The pressure of the compressed fluid in line 109 can be about 600 kPa, about 1,300 kPa, about 2,000 kPa, or about 2,700 kPa to about 1,700 kPa, about 2,500 kPa, about 3,000 kPa, about 3,500 kPa, or greater. In one or more embodiments, the compressor 105 can include one or more stages (two as shown 106, 108). In one or more embodiments, the compressor 105 can include one or more liquid and/or air cooled intercoolers between any two or more compressor stages. In one or more embodiments, shaft power can be supplied to the one or more compressors 105 via one or more electric motors, steam turbines, gas turbines, or any combination thereof.

The compressed fluid in line 109 can be introduced to the one or more scrubbers 110, where at least a portion of any acid gases present can be converted to one or more insoluble compounds and removed from the compressed fluid. A caustic solution can be introduced or otherwise flowed into the scrubber 110 via line 111. The caustic solution can have a pH of greater than 7, such as about 8 to about 14, or about 8.5 to about 12. In some example, the caustic solution can include an aqueous solution or mixture containing one or more of a hydroxide, a hypochlorite, ammonium, an amine, or other basic compounds. A spent caustic solution via line 114 can be recovered from the scrubber 110 for treatment, regeneration, and/or disposal and a scrubbed fluid via line 112 can be recovered from the scrubber 110. A spent caustic solution via line 114 can be recovered from the scrubber 110 for treatment, regeneration, and/or disposal. The operating pressure of the scrubber 110 can be about 600 kPa, about 1,300 kPa, about 1,700 kPa, about 2,000 kPa, about 2,500 kPa, or about 2,700 kPa to about 3,000 kPa, about 3,500 kPa, or greater. The operating temperature of the scrubber 110 can be about 0° C., about 5° C., about 10° C., or about 15° C. to about 75° C., about 80° C., about 90° C., or about 100° C.

The scrubber 110 can include one or more systems, devices or any combination of systems and/or devices suitable for removing all or a portion of the one or more acid gases in the compressed fluid in line 109 to provide a low (or reduced) acid concentration compressed fluid via line 112 and the spent caustic solution via line 114. The acid concentration in the compressed fluid in line 114 can be about 5 mol % or less, about 3 mol % or less, about 1 mol % or less, about 0.5 mol % or less, about 0.1 mol %, or less. The scrubber 110 can include one or more recirculation systems for recirculation of the caustic scrubbing solution through the scrubber 110. The scrubber 110 can be a vertical column having a length over diameter (L/D) ratio greater than 1, greater than 5, or greater than 10. In one or more embodiments, all or a portion of the interior of the scrubber 110 can be filled with trays and/or packing to increase the effective mass transfer area within the scrubber 110. In one or more embodiments, all or a portion of the interior of the scrubber 110 can be empty, that is without trays or packing.

The scrubbed fluid in line 112 can be introduced to the drier 120, where at least a portion of any water present in the scrubbed fluid can be removed to provide a recovered water via line 124 and an at least partially dried fluid via line 122. The drier 120 can include one or more deliquescent driers, regenerative desiccant driers, refrigeration driers, membrane driers, or any combination thereof. The dried fluid exiting the drier via line 122 can have a dew point of about 0° C. or less, about −20° C. or less, about −40° C. or less, about −80° C. or less, about −100° C., or less. The temperature of the dried fluid in line 122 can be about 500 kPa, about 1,000 kPa, about 1,400 kPa, or about 1,800 kPa to about 1,700 kPa, about 2,500 kPa, about 3,000 kPa, about 3,500 kPa, or greater.

In one or more embodiments, the dried fluid in line 122 can be introduced to the vapor-liquid separator 125 to provide an overhead via line 126 and bottoms via line 128. In some embodiments, the vapor-liquid separator can be a "depropanizer" and the bottoms via line 128 can include $C_4$ and heavier hydrocarbons and the overhead via line 126 can include $C_3$ and lighter hydrocarbons. In other embodiments, the vapor-liquid separate can be a "deethanizer" and the bottoms via line 128 can include one or more $C_3$ and heavier hydrocarbons and the overhead via line 126 can include $C_1$ and $C_2$ hydrocarbons. For simplicity and ease of description, the system 100 will be further discussed and describe in the context of 125 as a depropanizer. The operating pressure of the depropanizer 125 can be about 500 kPa, about 1,000 kPa, about 1,400 kPa, about 1,500 kPa, or about 1,600 kPa to about 1,700 kPa, about 1,800 kPa, about 2,500 kPa, about 3,000 kPa, about 3,500 kPa, or greater. The operating temperature of the depropanizer 125 can be about −73° C., about −65° C., about −60° C., about −55° C., about −53° C., about −50° C., about −48° C., about −45° C., about −43° C., about −40° C., about −38° C., about −35° C., about −33° C., about −30° C., about −27° C., about −25° C., or about −23° C. to about −20° C., about −17° C., about −15° C., about −13° C., about −10° C., about −8° C., about −5° C., about −3° C., about 0° C., about 5° C., about 10° C., about 12° C., about 15° C., or about 17° C.

In some embodiments, the $C_4$ and heavier hydrocarbons via line 128 can include, but are not limited to, butane, butene, butylene, pentane, pentene, isomers thereof, unsaturated derivatives thereof, or any mixture thereof. In an alternative embodiment, the $C_3$ and heavier hydrocarbons via line 128 can include, but are not limited to, propane, propylene, butane, butene, butylene, pentane, pentene, isomers thereof, unsaturated derivatives thereof, or any mixture thereof. In one or more embodiments, all or a portion of the $C_3$ and heavier hydrocarbons or the $C_4$ and heavier hydrocarbons in line 128 can be recycled to a pyrolytic or other process used to produce at least a portion of the hydrocarbon in line 102. The pressure of the $C_3$ and heavier hydrocarbons or the $C_4$ and heavier hydrocarbons in line 128 can be about 300 kPa, about 500 kPa, about 600 kPa, or about 700 kPa to about 1,700 kPa, about 2,100 kPa, about 2,500 kPa, about 3,000 kPa, or greater. The temperature of the $C_3$ and heavier hydrocarbons or the $C_4$ and heavier hydrocarbons in line 128 can be about −60° C., about −50° C., or about −40° C., to about 0° C., about 10° C., about 20° C., or about 30° C.

In one or more embodiments, the depropanizer 125 can include one or more systems, devices, or any combination of systems and/or devices suitable for selectively separating $C_3$ and lighter hydrocarbons from a mixture containing one or more $C_1$ to $C_{20}$ hydrocarbons. The depropanizer 125 can be a vertical column having a length over diameter (L/D) ratio greater than 1, greater than 5, or greater than 10 in some embodiments. All or a portion of the interior of the depropanizer 125 can be filled with trays and/or packing to increase the effective mass transfer area within the depropanizer 125. All or a portion of the interior of the depropanizer 125 can be empty, that is without trays or packing. One or more condensers can be located internal or external to the depropanizer 125. One or more reboilers can be located internal or external to the depropanizer 125.

The overhead in line 126 can include, but is not limited to, hydrogen, methane, ethane, ethylene, acetylene, propane, propylene, isomers thereof, or any mixture thereof. The hydrogen concentration in the overhead in line 126 can be about 0.1 mol %, about 0.5 mol %, about 1 mol %, or about 2 mol % to less than 5 mol %, less than 7 mol %, less than 10 mol %, or less than 15 mol %. The methane concentration in the overhead in line 126 can be about 0.1 mol % to less than 12 mol %, such as about 0.1 mol %, about 0.5 mol %, about 1 mol %, or about 2 mol % to about 3 mol %, about 5 mol %, about 7 mol %, or less than 12 mol %. The ethane concentration in the overhead in line 126 can be can be about 0.5 mol %, about 1 mol %, about 2 mol %, about 3 mol %, about 4 mol %, or less than 5 mol % to 5 mol %, less than 10 mol %, less than 15 mol %, or less than 25 mol %. The ethylene concentration in the overhead in line 126 can be about 0.5 mol %, about 1 mol %, about 2 mol %, about 3 mol %, about 4 mol %, or less than 5 mol % to 5 mol %, less than 10 mol %, less than 15 mol %, or less than 25 mol %. The acetylene concentration in the overhead in line 126 can be about 0.1 mol %, about 0.5 mol %, about 0.75 mol %, about 1 mol %, about 1.3 mol %, about 1.5 mol %, or about 2 mol % to about 2.5 mol %, about 3 mol %, less than 5 mol %, less than 7 mol %, or less than 10 mol %. The propane concentration in the overhead in line 126 can be about 0.5 mol %, about 1 mol %, about 1.5 mol %, about 2 mol %, about 3 mol %, about 4 mol %, or about 5 mol % to about 6 mol %, about 8 mol %, less than 10 mol %, less than 15 mol %, or less than 25 mol %. The propylene concentration in the overhead in line 126 can be about 0.5 mol %, about 1 mol %, about 2 mol %, about 3 mol %, about 4 mol %, or less than 5 mol % to 5 mol %, less than 10 mol %, less than 15 mol %, or less than 25 mol %.

The overhead in line 126 can be at a pressure of about 400 kPa, about 600 kPa, about 800 kPa, or about 900 kPa to about 1,700 kPa, about 2,000 kPa, about 2,500 kPa, or about 3,000 kPa. The overhead in line 126 can be at a temperature of about −73° C., about −65° C., about −60° C., about −55° C., about −53° C., about −50° C., about −48° C., about −45° C., about −43° C., about −40° C., about −38° C., about −35° C., about −33° C., about −30° C., about −27° C., about −25° C., or about −23° C. to about −20° C., about −17° C., about −15° C., about −13° C., about −10° C., about −8° C., about −5° C., about −3° C., about 0° C., about 5° C., about 10° C., about 12° C., about 15° C., or about 17° C.

The overhead via line 126 can be introduced to the compressor 130 to provide a compressed fluid via line 132. The pressure of the overhead in line 126 can be increased by about 1,500 kPa or greater, about 2,000 kPa or greater, about 2,500 kPa or greater, or about 3,000 kPa or greater, by passage through the one or more compressors 130. The compressed fluid in line 132 can be at a pressure of about 1,900 kPa, about 2,100 kPa, about 2,300 kPa, or about 2,400 kPa to about 4,700 kPa, about 5,000 kPa, about 5,500 kPa, about 6,000 kPa, or greater.

The compressor 130 can include one or more systems, devices, or combination of systems and/or devices suitable for compressing a fluid at a first pressure to provide a fluid at a second pressure, where the second pressure is greater than the first pressure. The compressor 130 can include one or more stages, two or more separate and independent compressors, or a combination thereof. The compressor 130 can include one or more intercoolers between any two or more compressors and/or compressor stages. Shaft power can be supplied to the one or more compressors 130 via one or more electric motors, steam turbines, gas turbines, or any combination thereof.

The compressed fluid via line 132 can be introduced to the reactor system ("acetylene converter") 135, where at least a portion of any acetylene present in the compressed fluid can be converted to ethane and/or ethylene to provide a hydrogenated mixture via line 136. Hydrogen can be introduced via line 138 to the compressed fluid in line 132 prior to introducing the compressed fluid to the acetylene converter 135 or the hydrogen can be introduced directly to the acetylene converter 135. The hydrogen introduced via line 138 can be about 50 mol % hydrogen or greater, about 75 mol % hydrogen or greater, about 90 mol % hydrogen or greater, about 95 mol % hydrogen or greater, about 99 mol % hydrogen or greater, or about 99.9 mol % hydrogen or greater. The hydrogen in 138 can contain carbon monoxide and/or carbon dioxide.

In one or more embodiments, about 75%, about 80%, about 90%, about 95%, about 99%, or about 99.9% of the acetylene present in the compressed process fluid in line 132 can be converted to ethane and/or ethylene in the acetylene converters 135. The acetylene concentration in the hydrogenated mixture via line 136 can be about 1 mol % or less, about 0.5 mol % or less, about 0.1 mol % or less, about 0.05 mol % or less, about 0.03 mol % or less, about 0.01 mol %, or less. The pressure of the hydrogenated mixture in line 136 can be about 1,100 kPa, about 1,300 kPa, about 1,400 kPa, or about 1,500 kPa to about 4,200 kPa, about 4,400 kPa, about 4,700 kPa, about 5,200 kPa, or greater.

The one or more acetylene converters 135 can include one or more systems, devices or combination of systems and/or devices suitable for converting at least a portion of any acetylene present in the compressed process fluid in line 132 to ethane and ethylene. The one or more acetylene converters 135 can contain one or more catalyst beds. The one or more catalyst beds can be fixed beds, fluidized beds, ebullating beds, slurry beds, moving beds, bubbling beds, any other suitable type of catalyst bed, or any combination thereof. The one or more acetylene converters 135 can include one or more dual-bed converter systems such as those discussed and described in U.S. Pat. No. 7,038,097. The catalyst within the acetylene converter 135 can include, but is not limited to, one or more nickel based catalysts, such as Ni/NiAl$_2$O$_4$, one or more palladium based catalysts, such as Pd/PdAl$_2$O$_3$, alloys thereof, derivatives thereof, combinations thereof, or any mixture thereof.

The hydrogenated mixture via line 136 can be introduced to the chilling system 200 to provide a cooled hydrogenated mixture via lines 142 and/or 147. The chilling system 200 can include a first cooler 140 and a second cooler 145. The first cooler 140 can condense at least a portion of the hydrogenated mixture, which can be recovered via line 142. Non-condensed hydrogenated mixture can be recovered via line 144 from the first cooler 140, which can be introduced to the second cooler 145 to provide a condensed hydrogenated mixture via line 147 and tail gases via lines 149 and 151. A hydrogen-rich tail gas can be recovered via line 149 and a hydrogen-lean tail gas can be recovered via line 151. In some embodiments, the hydrogen-lean tail gas recovered via line 151, or any other fluid or composition, can be recycled or otherwise flowed via line 152 (e.g., a bypass line) to the compressor 105, such as to line 107 disposed downstream of the first stage 106 and upstream of the second stage 108, as depicted in FIG. 1. Alternatively, although not show, the hydrogen-lean tail gas or other fluid or composition via line 152 can be recycled or otherwise flowed upstream of the first stage 106, such as to line 102 or downstream of the second stage 108, such as to line 109.

The first cooler 140 and/or the second cooler 145 can cool the hydrogenated mixture introduced via line 136 using any suitable heat transfer medium or combination of heat transfer mediums. Illustrative heat transfer mediums that can be used to cool the hydrogenated mixture introduced to the first cooler 140 can include, but are not limited to, ethylene, propylene, cooling water, air, any combination thereof, or any mixture thereof. Illustrative heat transfer mediums that can be used to cool the non-condensed hydrogenated mixture introduced via line 144 to the second cooler 145 can include, but are not limited to, propylene. The first cooler 140, the second cooler 145, or both can use refrigerated propylene as the heat transfer medium. The use of refrigerated ethylene to cool the hydrogenated mixture is not required. In one or more embodiments, refrigerated propylene at a temperature of about 5° C., about 0° C., about −5° C., about −10° C., about −20° C., about −30° C., about −40° C., or less can be used to indirectly cool the hydrogenated mixture introduced via line 136 to the chilling system 200.

The chilling system 200 can include any suitable system, device, or combination of systems and/or devices for cooling the hydrogenated mixture in line 136. The chilling system 200 can include one or more heat exchangers. For example, the chilling system 200 can include, but is not limited to, one or more shell-and-tube heat exchangers, core-type heat exchangers, plate and frame heat exchangers, spiral wound heat exchangers, U-tube heat exchangers, and/or bayonet style heat exchangers. The one or more heat exchangers can include surface enhanced tubes (e.g., fins, static mixers, rifling, heat conductive packing, turbulence causing projections, or any combination thereof), and the like.

In one or more embodiments, at least a portion of the condensed hydrogenated mixture via line 142 and/or line 147 can be introduced to the vapor-liquid separator ("demethanizer") 155 to provide a methane-rich overhead via line and methane-lean bottoms via line 159. In one or more embodiments, at least a portion of the condensed hydrogenated mixture in line 142 can be recycled via line 143 to the depropanizer 125 as a reflux. In one or more embodiments, at least a portion of the condensed hydrogenated mixture in line 147 can be recycled via line 148 to the compressor 105. As illustrated, a portion of the hydrogenated mixture in line 147 can be recycled via line 148 to the first stage 106 and/or a portion can be recycled to the second stage 108.

In one or more embodiments, at least a portion of the methane-rich overhead via line 157 can be recycled to the compressor 130. In one or more embodiments, all or a portion of the methane-rich overhead via line 157 can be recovered as a product, which can be further processed or used as fuel, for example.

The operating pressure of the demethanizer 155 can be about 600 kPa, about 700 kPa, about 800 kPa, or about 900 kPa to about 2,500 kPa, about 2,700 kPa, about 2,900 kPa, about 3,500 kPa, about 4,000 kPa, or about 4,200 kPa. The operating temperature of the demethanizer 155 can be greater than the boiling point of propylene (e.g., about −48.1° C.). The operating temperature of the demethanizer 155 can be about −48° C., about −45° C., about −43° C., about −40° C., about −38° C., about −35° C., about −33° C., about −30° C., about −27° C., about −25° C., or about −23° C., about −20° C., about −17° C., about −15° C., or about −13° C. to about −10° C., about −7° C., about −5° C., about −3° C., about 0° C., about 5° C., about 10° C., about 12° C., about 15° C., or about 17° C.

The demethanizer 155 can include one or more systems, devices, or any combination of systems and/or devices suitable for providing the methane-rich overhead via line 157 and the methane-lean bottoms via line 159. The demethanizer 155 can be a vertical column having a length over diameter (L/D) ratio greater than 1, greater than 5, or greater than 10. All or a portion of the interior of the demethanizer 155 can be filled with trays and/or packing to increase the effective mass transfer area within the demethanizer 155. All or a portion of the interior of the demethanizer 155 can be empty, that is without trays or packing. One or more condensers can be located internal or external to the demethanizer 155. One or more reboilers can be located internal or external to the demethanizer 155.

The methane-lean bottoms via line 159 can be introduced to the vapor-liquid separator ("deethanizer") 160 to provide a $C_2$-rich overhead via line 161 and a $C_2$-lean bottoms via line 163. The operating pressure of the deethanizer 160 can be about 400 kPa, about 600 kPa, about 800 kPa, about 900 kPa, about 1,000 kPa, about 1,200 kPa, or about 1,400 kPa to about 1,700 kPa, about 2,000 kPa, about 2,500 kPa, about 3,000 kPa, about 3,500 kPa, or about 4,000 kPa. The operating temperature of the deethanizer 160 can be about −73° C., about −65° C., about −60° C., about −55° C., about −53° C., about −50° C., about −48° C., about −45° C., about −43° C., about −40° C., about −38° C., about −35° C., about −33° C., about −30° C., about −27° C., about −25° C., or about −23° C. to about −20° C., about −17° C., about −15° C., about −13° C., about −10° C., about −8° C., about −5° C., about −3° C., about 0° C., about 5° C., about 10° C., about 12° C., about 15° C., or about 17° C.

The ethane concentration in the $C_2$-rich overhead in line 161 can be about 3 mol %, about 9 mol %, about 18 mol %, or about 35 mol % to about 40 mol %, about 47 mol %, about 55 mol %, about 70 mol %, about 85 mol %, or about 97 mol %. The ethylene concentration in the $C_2$-rich overhead in line 161 can be about 3 mol %, about 9 mol %, about 18 mol %, or about 35 mol % to about 40 mol %, about 47 mol %, about 55 mol %, about 70 mol %, about 85 mol %, or about 97 mol %. The pressure of the $C_2$-rich overhead in line 161 can be about 400 kPa, about 500 kPa, about 600 kPa, or about 700 kPa to about 3,500 kPa, about 3,800 kPa, about 4,500 kPa, or about 4,800 kPa. The temperature of the $C_2$-rich overhead in line 161 can be about −83° C., about −80° C., about −77° C., about −75° C., about −73° C., about −65° C., about −60° C., about −55° C., about −53° C., about −50° C., about −48° C., about −45° C., about −43° C., about −40° C., about −38° C., about −35° C., about −33° C., about −30° C., about −27° C., about −25° C., or about −23° C. to about −20° C., about −17° C., about −15° C., about −13° C., about −10° C., about −8° C., about −5° C., about −3° C., about 0° C., about 5° C., about 10° C., about 12° C., about 15° C., or about 17° C.

The $C_2$-lean bottoms in line 163 can include, but is not limited to, propane, propylene, methylacetylene (propyne), and/or propadiene. The propane concentration in the $C_2$-lean bottoms in line 163 can be about 5 mol %, about 10 mol %, about 20 mol %, or about 40 mol % to about 50 mol %, about 60 mol %, about 80 mol %, or about 95 mol %. The propylene concentration in the $C_2$-lean bottoms in line 163 can be about 5 mol %, about 10 mol %, about 20 mol %, or about 40 mol % to about 50 mol %, about 60 mol %, about 80 mol %, or about 95 mol %. The methylacetylene concentration in the $C_2$-lean bottoms in line 163 can be about 0.1 mol %, about 0.3 mol %, about 0.5 mol %, or about 0.7 mol % to about 1.5 mol %, about 1.7 mol %, about 2 mol %, or about 2.5 mol %. The propadiene concentration in the $C_2$-lean bottoms in line 163 can be about 1 mol %, about 1.5 mol %, about 2 mol %, or about 2.5 mol % to about 4 mol %, about 4.5 mol %, about 5 mol %, or about 6 mol %.

The deethanizer 160 can include one or more systems, devices, or any combination of systems and/or devices suitable for providing the $C_2$-rich overhead via line 161 and the $C_2$-lean bottoms via line 163. In some examples, the deethanizer 160 can provide the $C_2$-rich overhead via line 161 and the $C_2$-lean bottoms via line 163. The deethanizer 160 can include a vertical column having a length over diameter (L/D) ratio greater than 1, greater than 5, or greater than 10. All or a portion of the interior of the deethanizer can be filled with trays and/or packing to increase the effective mass transfer area within the deethanizer. All or a portion of the interior of the deethanizer can be empty that is without trays or packing. One or more condensers can be located internal or external to the deethanizer. One or more reboilers can be located internal or external to the deethanizer.

The $C_2$-rich overhead via line 161 can be introduced to the vapor-liquid separator ("$C_2$ splitter") 175 to provide an ethylene-rich overhead ("first product") via line 176 and an ethane-rich bottoms ("second product") via line 178. The operating pressure within the $C_2$-splitter 175 can be about 360 kPa, about 400 kPa, about 600 kPa, about 800 kPa, about 1,000 kPa, about 1,200 kPa, about 1,400 kPa, about 1,600 kPa, about 1,800 kPa, about 2,000 kPa, or about 2,200 kPa to about 2,500 kPa, about 2,700 kPa, about 3,000 kPa, about 3,300 kPa, about 3,500 kPa, about 3,700 kPa, or about 4,000 kPa. For example, the pressure within the $C_2$-splitter 175 can be about 360 kPa to about 4,000 kPa, about 500 kPa to about 3,500 kPa, about 900 kPa to about 3,000 kPa, or about 1,300 kPa to about 2,600 kPa.

In one or more embodiments, the first product or ethylene can be separated from the second hydrocarbon mixture at a pressure of about 360 kPa, about 400 kPa, about 450 kPa, about 500 kPa, about 550 kPa, about 600 kPa, about 700 kPa, about 750 kPa, about 800 kPa, about 850 kPa, about 900 kPa, about 950 kPa, about 1,000 kPa, about 1,050 kPa, about 1,100 kPa, about 1,150 kPa, about 1,200 kPa, about 1,250 kPa, about 1,300 kPa, about 1,350 kPa, about 1,400 kPa, about 1,450 kPa, or about 1,500 kPa to about 2,000 kPa, about 2,100 kPa, about 2,200 kPa, about 2,300 kPa, about 2,400 kPa, about 2,500 kPa, about 2,600 kPa, about 2,700 kPa, about 2,800 kPa, about 2,900 kPa, about 3,000 kPa, about 3,100 kPa, about 3,200 kPa, about 3,300 kPa, about 3,400 kPa, about 3,500 kPa, about 3,600 kPa, about 3,700 kPa, about 3,800 kPa, about 3,900 kPa, or about 4,000 kPa. In one or more embodiments, the first product or ethylene can be separated from the second hydrocarbon mixture at a pressure of at least 360 kPa, at least 400 kPa, at least 450 kPa, at least 500 kPa, at least 550 kPa, at least 600 kPa, at least 700 kPa, at least 750 kPa, at least 800 kPa, at least 850 kPa, at least 900 kPa, at least 950 kPa, at least 1,000 kPa, at least 1,050 kPa, at least 1,100 kPa, at least 1,150 kPa, at least 1,200 kPa, at least 1,250 kPa, at least 1,300 kPa, at least 1,350 kPa, at least 1,400 kPa, at least 1,450 kPa, or at least 1,500 kPa, to less than 2,000 kPa, less than 2,100 kPa, less than 2,200 kPa, less than 2,300 kPa, less than 2,400 kPa, less than 2,500 kPa, less than 2,600 kPa, less than 2,700 kPa, less than 2,800 kPa, less than 2,900 kPa, less than 3,000 kPa, less than 3,100 kPa, less than 3,200 kPa, less than 3,300 kPa, less than 3,400 kPa, less than 3,500 kPa, less than 3,600 kPa, less than 3,700 kPa, less than 3,800 kPa, less than 3,900 kPa, or less than 4,000 kPa.

The operating temperature of the $C_2$-splitter 175 can be greater than the boiling point of propylene (e.g., about −48.1° C.). In one or more embodiments, the first product or ethylene can be separated from the second hydrocarbon mixture at a temperature of about −48° C., about −47° C., about −46° C., about −45° C., about −44° C., about −43° C., about −42° C., about −41° C., about −40° C., about −39° C., about −38° C., about −37° C., about −36° C., about −35° C., about −34° C., about −33° C., about −32° C., about −31° C., about −30° C., about −29° C., about −28° C., about −27° C., about −26° C., about −25° C., about −24° C., about −23° C., about −22° C., about −21° C., about −20° C., about −19° C., about −18° C., about −17° C., about −16° C., about −15° C., about −14° C., or about −13° C. to about −10° C., about −7° C., about −5° C., about −3° C., about 0° C., about 3° C., about 5° C., about 7° C., about 10° C., about 12° C., about 14° C., or about 17° C. In one or more embodiments, the first product or ethylene can be separated from the second hydrocarbon mixture at a temperature of greater than −48° C., greater than −45° C., greater than −43° C., greater than −41° C., greater than −38° C., greater than −35° C., greater than −33° C., greater than −30° C., greater than −27° C., greater than −25° C., greater than −23° C., greater than −20° C., greater than −17° C., greater than −15° C., or greater than −13° C. to less than −10° C., less than −7° C., less than −5° C., less than −3° C., less than 0° C., less than 3° C., less than 5° C., less than 7° C., less than 10° C., less than 12° C., less than 14° C., or less than 17° C.

The ethylene concentration of the first product in line 176 can be greater than 85 mol %, greater than 87 mol %, greater than 90 mol %, greater than 92 mol %, greater than 93 mol %, greater than 94 mol %, greater than 95 mol %, greater than 96 mol %, greater than 97 mol %, greater than 98 mol %, greater than 98.5 mol %, greater than 99 mol %, greater than 99.5 mol %, or greater than 99.9 mol %. The pressure of the first product in line 176 can be about 400 kPa, about 500 kPa, about 600 kPa, or about 700 kPa to about 2,500 kPa, about 2,700 kPa, about 3,300 kPa, or about 4,000 kPa. The temperature of the first product in line 176 can be about −48° C., about −45° C., about −43° C., about −40° C., about −38° C., about −35° C., about −33° C., about −30° C., about −27° C., about −25° C., about −23° C., about −20° C., about −17° C., about −15° C., or about −13° C. to about −10° C., about −7° C., about −5° C., about −3° C., about 0° C., about 3° C., about 5° C., about 7° C., about 10° C., about 13° C., about 15° C., or about 17° C.

The ethane concentration in the second product in line 178 can be greater than 85 mol %, greater than 87 mol %, greater than 90 mol %, greater than 92 mol %, greater than 93 mol %, greater than 94 mol %, greater than 95 mol %, greater than 96 mol %, greater than 97 mol %, greater than 98 mol %, greater than 98.5 mol %, greater than 99 mol %, greater than 99.5 mol %, or greater than 99.9 mol %. The pressure of the second product in line 178 can be about 400 kPa, about 500 kPa, about 600 kPa, or about 700 kPa to about 2,500 kPa, about 2,700 kPa, about 3,300 kPa, or about 4,000 kPa. The temperature of the second product in line 178 can be about −48° C., about −45° C., about −43° C., about −40° C., about −38° C., about −35° C., about −33° C., about −30° C., about −27° C., about −25° C., about −23° C., about −20° C., about −17° C., about −15° C., or about −13° C. to about −10° C., about −7° C., about −5° C., about −3° C., about 0° C., about 3° C., about 5° C., about 7° C., about 10° C., about 13° C., about 15° C., or about 17° C.

The one or more $C_2$-splitters 175 can include one or more systems, devices, or any combination of systems and/or devices suitable for providing an overhead containing ethylene and a bottoms containing ethane. The $C_2$-splitter 190 can be a vertical column having a length over diameter (L/D) ratio greater than 1, greater than 5, or greater than 10. All or a portion of the interior of the $C_2$-splitter 190 can be filled with trays and/or packing to increase the effective mass transfer area within the $C_2$-splitter 190. All or a portion of the interior of the $C_2$-splitter 190 can be empty, that is without trays or packing. One or more condensers can be located internal or external to the $C_2$-splitter 190. One or more reboilers can be located internal or external to the $C_2$-splitter 190.

In one or more embodiments, all or a portion of the second product in line 178 can be recycled to the pyrolytic process used to provide all or a portion of the hydrocarbon in line 102. For example, about 5% or more, about 25% or more, about 50% or more, about 75% or more, about 85% or more, about 90% or more, about 95% or more, about 99% or more, or about 99.9% or more of the second product in line 178 can be recycled to the pyrolytic process used to provide all or a portion of the hydrocarbon in line 102.

In one or more embodiments, the $C_2$-lean bottoms in line 163 can be introduced to the reactor system ("MAPD converter") 165 to provide a $C_2$-lean bottoms via line 167 having a reduced concentration of methylacetylene and/or propadiene. Hydrogen via line 164 can be introduced to the MAPD converter 165. The methylacetylene and/or the propadiene present in the $C_2$-lean bottoms introduced via line 163 to the MAPD converter 165 can be converted to propylene. The hydrogen added via line 138 can be about 50 mol % hydrogen or greater, about 75 mol % hydrogen or greater, about 90 mol % hydrogen or greater, about 95 mol % hydrogen or greater, about 99 mol % hydrogen or greater, or about 99.9 mol % hydrogen or greater. The hydrogen added via line 138 can contain carbon monoxide and/or carbon dioxide.

In one or more embodiments, about 75%, about 80%, about 90%, about 95%, about 99%, or about 99.9% of the methylacetylene and/or propadiene present in the $C_2$-lean bottoms in line 163 can be converted to propylene in the MAPD converter 165. The methylacetylene concentration in the hydrogenated mixture via line 167 can be about 1 mol % or less, about 0.5 mol %, about 0.1 mol %, about 0.05 mol %, about 0.03 mol %, about 0.01 mol %, or less. The propadiene concentration in the hydrogenated mixture via line 167 can be about 1 mol % or less, about 0.5 mol %, about 0.1 mol %, about 0.05 mol %, about 0.03 mol %, about 0.01 mol %, or less.

The MAPD converter 165 can include one or more systems, devices or combination of systems and/or devices suitable for converting at least a portion of any methylacetylene and/or propadiene present in the $C_2$-lean bottoms in line 163 to propylene. In one or more embodiments, the MAPD converter 165 can contain one or more catalyst beds. In one or more embodiments, the one or more catalyst beds can be fixed beds, fluidized beds, ebullating beds, slurry beds, moving beds, bubbling beds, any other suitable type of catalyst bed, or combinations thereof. In one or more embodiments, the catalyst within the MAPD converter 165 can include, but is not limited to, one or more palladium-based based catalysts, such as available catalyst vendors such as Axens, CRI Catalyst Company, or Sud-Chemie, or any mixture thereof.

The $C_2$-lean bottoms via line 167 having a reduced concentration of methylacetylene and/or propadiene can be introduced to the vapor-liquid separator ("$C_3$ splitter") 170 to provide a propylene-rich overhead ("third product") via line 172 and a propane-rich bottoms ("fourth product") via line 174. Although not shown, in one or more embodiments, all or a portion of the fourth product in line 174 can be recycled to the pyrolytic process used to provide all or a portion of the hydrocarbon in line 102. In one or more embodiments, about 5% or more, about 25% or more, about 50% or more, about 75% or more, about 85% or more, about 90% or more, about 95% or more, about 99% or more, or about 99.9% or more of the fourth product in line 174 can be recycled to the pyrolytic process used to provide all or a portion of the hydrocarbon in line 102.

Figure 2:
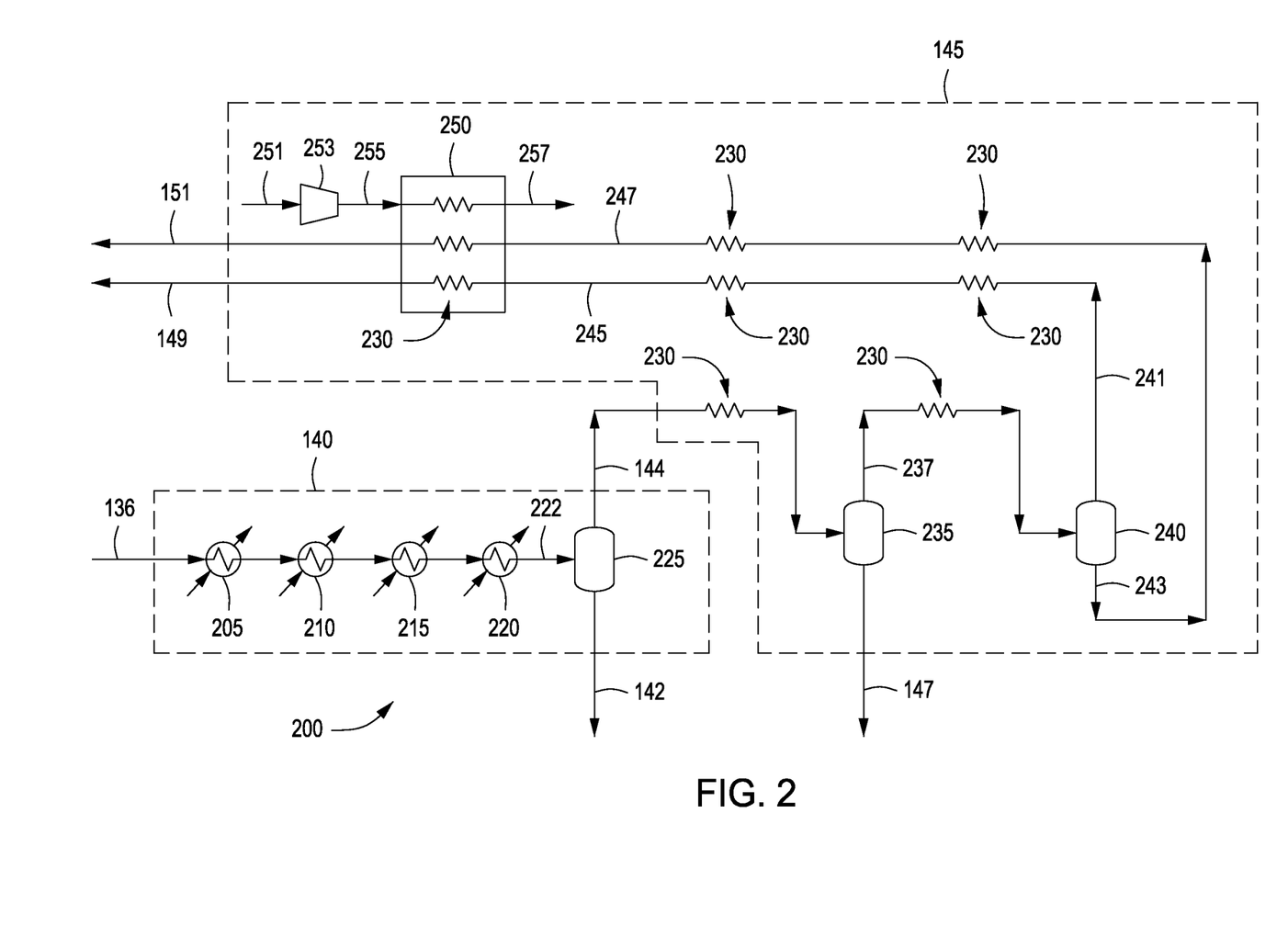
FIG. 2 depicts an illustrative cooling system shown in FIG. 1, according to one or more embodiments described.

FIG. 2 depicts the illustrative chilling system 200 shown in FIG. 1, according to one or more embodiments. The chilling system 200 can include the first cooler 140 and the second cooler 145, as discussed and described above with reference to FIG. 1. In one or more embodiments, the first cooler 140 can include one or more heat exchangers (four are shown 205, 210, 215, 220) and one or more vapor/liquid separators "knock-out drums" 225. In one or more embodiments, the second cooler 145 can include one or more heat exchangers 230 (nine are shown), one or more knock-out drums (two are shown 235, 240), and one or more multi-pass exchanger known typical in the industry as a coldbox 250. The heat exchangers 205, 210, 215, and 220 can be shell-and-tube heat exchangers and the heat exchanges 230 can be core-type heat exchangers. The multi-pass heat exchanger or the coldbox 250 can be or include one or more heat exchangers configured to cool and/or hear one or more streams using brazed aluminum heat transfer cores at least partially contained within an insulated box. For example, as shown the cold box 250 can include three heat exchangers 230.

The hydrogenated mixture via line 136 can be serially introduced to the heat exchangers 205, 210, 215, and 220 to provide an at least partially condensed hydrogenated mixture via line 222. Although not shown, the hydrogenated mixture via line 136 can be introduced in parallel, in series/parallel, and/or in parallel/series to two or more heat exchangers to provide the at least partially condensed hydrogenated mixture via line 222.

The at least partially condensed hydrogenated mixture via line 222 can be introduced to the knock-out drum 225 to provide the cooled hydrogenated mixture via line 142 and the gaseous hydrogenated mixture via line 144. The gaseous hydrogenated mixture via line 144 can be introduced to one or more of the heat exchangers 230 (one as shown) and the knock-out drum 235 to provide the condensed hydrogenated mixture via line 147 and a tail gas via line 237. The tail gas via line 237 can be introduced to one or more of the heat exchangers 230 (one as shown) and the knock-out drum 240 to provide a hydrogen-rich tail gas via line 241 and a hydrogen-lean tail gas via line 243.

In one or more embodiments, the hydrogen-rich tail gas via line 241 can be introduced through one or more heat exchangers 230 (two as shown) to provide a heated hydrogen-rich tail gas via line 245. In one or more embodiments, the hydrogen-lean tail gas via line 243 can be introduced through one or more heat exchangers 230 (two as shown) to provide a heated hydrogen-lean tail gas via line 247. The hydrogen-rich tail gas via line 245 and the hydrogen-lean tail gas via line 247 can be introduced to the coldbox 250 to provide the hydrogen-rich tail gas via line 149 and the hydrogen-lean tail gas via line 151, as shown in FIG. 1.

In one or more embodiments, propylene via line 251 can be introduced to one or more compressors 253 to provide a compressed propylene via line 255. In one or more embodiments, the pressure of the propylene in line 251 can be increased by about 1,500 kPa or greater, about 2,000 kPa or greater, about 2,500 kPa or greater, or about 3,000 kPa or greater by passage through the one or more compressors 253. The compressed propylene in line 255 can be at a temperature of about 40° C., about 45° C., about 50° C., or about 55° C. to about 80° C., about 85° C., about 90° C., or about 95° C. Although not shown, in one or more embodiments, the compressed propylene from the compressor 253 can be cooled via indirect heat exchange to provide the compressed propylene via line 255.

The compressor 253 can include one or more systems, devices, or combination of systems and/or devices suitable for compressing a fluid at a first pressure to provide a fluid at a second pressure, where the second pressure is greater than the first pressure. The compressor 253 can include one or more stages, two or more separate and independent compressors, or a combination thereof. The compressor 253 can include one or more intercoolers between any two or more compressors and/or compressor stages. Shaft power can be supplied to the one or more compressors 253 via one or more electric motors, steam turbines, gas turbines, or any combination thereof.

In one or more embodiments, propylene via line 255 can be introduced to the coldbox 250, where heat can be indirectly transferred from the propylene to the hydrogen-rich tail gas and/or the hydrogen-lean tail gas introduced via lines 245 and 247, respectively. The cooled propylene via line 257 can be recovered from the coldbox 250.

In one or more embodiments, at least a portion of the hydrogen-lean tail gas via line 151 can be recycled to the compressor 105. For example, at least a portion of the hydrogen-lean tail gas via line 151 can be recycled to the second stage 108 of the compressor 105. In one or more embodiments, the hydrogen-rich tail gas via line 149 can be recovered from the chilling system 200 as a product. In one or more embodiments, the hydrogen-rich tail gas via line 151 can be introduced to the one or more reactor systems 135 and/or 165 via lines 138 and 164, respectively.

Embodiments of the present disclosure further relate to any one or more of the following paragraphs:

1. A method for separating one or more olefins comprising: separating at least a portion of one or more $C_3$ and heavier hydrocarbons from a hydrocarbon comprising $C_1$ to $C_{20}$ hydrocarbons to provide a first hydrocarbon mixture comprising methane, ethane, ethylene, and acetylene; hydrogenating at least a portion of the first hydrocarbon mixture to convert at least a portion of the acetylene to ethane and ethylene; separating at least a portion of the methane from the hydrogenated mixture to provide a second hydrocarbon mixture comprising ethane and ethylene; and separating at least a portion of the ethylene from the second hydrocarbon mixture to provide a first product comprising at least 95 mol % ethylene and a second product comprising at least 95 mol % ethane, wherein the ethylene is separated from the second hydrocarbon mixture at a pressure of about 360 kPa to about 4,000 kPa.

2. The method according to paragraph 1, further comprising transferring at least a portion of the second product to a pyrolysis furnace.

3. The method according to paragraph 1 or 2, wherein the one or more $C_3$ and heavier hydrocarbons are separated from the hydrocarbon comprising $C_1$ to $C_{20}$ hydrocarbons at a pressure of about 400 kPa to about 3,000 kPa.

4. The method according to any one of paragraphs 1 to 3, wherein the methane is separated from the hydrogenated mixture at a pressure of about 600 kPa to about 4,200 kPa, and the ethylene is separated from the second hydrocarbon mixture at a pressure of about 500 kPa to about 2,500 kPa.

The method according to any one of paragraphs 1 to 4, wherein at least a portion of the hydrocarbon comprising $C_1$ to $C_{20}$ hydrocarbons is produced by cracking a heavy hydrocarbon containing $C_4+$ hydrocarbons in a fluid catalytic cracker, a pyrolytic process, or combination thereof.

6. The method according to any one of paragraphs 1 to 5, wherein the one or more $C_3$ and heavier hydrocarbons are separated from the hydrocarbon comprising $C_1$ to $C_{20}$ hydrocarbons at a pressure of about 800 kPa to about 2,000 kPa, the methane is separated from the hydrogenated mixture at a pressure of about 900 kPa to about 3,500 kPa, and the ethylene is separated from the second hydrocarbon mixture at a pressure of about 500 kPa to about 2,500 kPa.

7. The method according to any one of paragraphs 1 to 6, wherein the first hydrocarbon mixture is hydrogenated in the presence of a catalyst.

8. The method according to any one of paragraphs 1 to 7, wherein the methane concentration in the hydrocarbon comprising $C_1$ to $C_{20}$ hydrocarbons is less than 12 mol %.

9. A method for separating one or more olefins comprising: compressing a gas comprising one or more $C_1$-$C_{20}$ hydrocarbons, water, one or more acid gases, and hydrogen; scrubbing at least a portion of the compressed fluid to remove at least a portion of the one or more acid gases; separating at least a portion of the water from the compressed fluid to provide a dehydrated fluid containing less than 0.5 mol % water, wherein the dehydrated fluid comprises the one or more $C_1$-$C_{20}$ hydrocarbons; separating at least a portion of one or more $C_4$ and heavier hydrocarbons from the dehydrated fluid to provide a hydrocarbon comprising one or more $C_1$-$C_3$ hydrocarbons; separating at least a portion of one or more $C_3$ hydrocarbons from the hydrocarbon comprising one or more $C_1$-$C_3$ hydrocarbons to provide a first hydrocarbon mixture comprising ethane, ethylene, acetylene, and methane; hydrogenating at least a portion of the first hydrocarbon mixture to convert at least a portion of the acetylene to ethane and ethylene; separating at least a portion of the methane from the hydrogenated mixture to provide a second hydrocarbon mixture comprising ethane and ethylene; and separating at least a portion of the ethylene from the second hydrocarbon mixture to provide a first product comprising at least 95 mol % ethylene and a second product comprising at least 95 mol % ethane, wherein the ethylene is separated from the second hydrocarbon mixture at a pressure of about 360 kPa to about 4,000 kPa.

10. The method according to paragraph 9, further comprising transferring all or a portion of the second product to a pyrolysis furnace.

11. The method according to paragraph 9 or 10, wherein the gas has a methane concentration of less than 15 mol %.

12. The method according to any one of paragraphs 9 to 11, wherein the gas has a hydrogen concentration of less than 15 mol %.

13. The method according to any one of paragraphs 9 to 12, wherein the one or more $C_4$ and heavier hydrocarbons are separated from the dehydrated fluid at a pressure of about 500 kPa to about 3,500 kPa.

14. The method according to any one of paragraphs 9 to 13, wherein the one or more $C_3$ hydrocarbons are separated from the hydrocarbon comprising one or more $C_1$-$C_3$ hydrocarbons at a pressure of about 400 kPa to about 3,000 kPa.

15. The method according to any one of paragraphs 9 to 14, wherein at least a portion of the hydrocarbon comprising one or more $C_1$-$C_3$ hydrocarbons is produced by cracking a heavy hydrocarbon containing $C_4+$ hydrocarbons in a fluid catalytic cracker, a pyrolytic process, or a combination thereof.

16. The method according to any one of paragraphs 9 to 15, wherein the ethylene is separated from the second hydrocarbon mixture at a pressure of about 500 kPa to about 2,500 kPa.

17. The method according to any one of paragraphs 9 to 16, wherein the one or more $C_3$ and heavier hydrocarbons are separated from the hydrocarbon comprising $C_1$ to $C_{20}$ hydrocarbons at a pressure of about 800 kPa to about 2,000 kPa, the methane is separated from the hydrogenated mixture at a pressure of about 900 kPa to about 3,500 kPa, and the ethylene is separated from the second hydrocarbon mixture at a pressure of about 500 kPa to about 2,500 kPa.

18. A system for producing one or more olefins comprising: one or more first separators for separating at least a portion of one or more $C_3$ and heavier hydrocarbons from a hydrocarbon comprising $C_1$ to $C_{20}$ hydrocarbons to provide a first hydrocarbon mixture comprising ethane, ethylene, and acetylene; one or more hydrogenators for hydrogenating at least a portion of the first hydrocarbon mixture to convert at least a portion of the acetylene to ethane and ethylene; one or more second separators for separating at least a portion of the methane from the hydrogenated mixture to provide a second hydrocarbon mixture comprising ethane and ethylene; and one or more third separators for separating at least a portion of the ethylene from the second hydrocarbon mixture at a pressure of about 360 kPa to about 4,000 kPa to provide a first product comprising at least 95 mol % ethylene and a second product comprising at least 95 mol % ethane.

19. The system according to paragraph 18, further comprising a recycle line for transferring at least a portion of the second product to a pyrolysis furnace.

20. The system according to paragraph 18 or 19, wherein the methane concentration of the hydrocarbon comprising $C_1$ to $C_{20}$ hydrocarbons is less than 12 mol %.

21. A system for producing one or more olefins comprising: means for separating at least a portion of one or more $C_3$ and heavier hydrocarbons from a hydrocarbon comprising $C_1$ to $C_{20}$ hydrocarbons to provide a first hydrocarbon mixture comprising ethane, ethylene, and acetylene; means for hydrogenating at least a portion of the first hydrocarbon mixture to convert at least a portion of the acetylene to ethane and ethylene; means for separating at least a portion of the methane from the hydrogenated mixture to provide a second hydrocarbon mixture comprising ethane and ethylene; and means for separating at least a portion of the ethylene from the second hydrocarbon mixture at a pressure of about 360 kPa to about 4,000 kPa to provide a first product comprising at least 95% mol ethylene and a second product comprising at least 95% mol ethane.

22. The system according to paragraph 21, further comprising a means for transferring all or a portion of the second product to a pyrolysis furnace.

23. The system according to paragraph 22, wherein the methane concentration of the hydrocarbon comprising $C_1$ to $C_{20}$ hydrocarbons is less than 12% mol.

24. The method or system according to any one of paragraphs 1 to 23, wherein the ethylene is separated from the second hydrocarbon mixture at a pressure of about 400 kPa to about 4,000 kPa.

25. The method or system according to any one of paragraphs 1 to 24, wherein the ethylene is separated from the second hydrocarbon mixture at a pressure of about 600 kPa to about 4,000 kPa.

26. The method or system according to any one of paragraphs 1 to 25, wherein the ethylene is separated from the second hydrocarbon mixture at a pressure of about 800 kPa to about 4,000 kPa.

27. The method or system according to any one of paragraphs 1 to 26, wherein the ethylene is separated from the second hydrocarbon mixture at a pressure of about 1,000 kPa to about 4,000 kPa.

The method or system according to any one of paragraphs 1 to 27, wherein the ethylene is separated from the second hydrocarbon mixture at a pressure of about 1,400 kPa to about 4,000 kPa.

29. The method or system according to any one of paragraphs 1 to 28, wherein the ethylene is separated from the second hydrocarbon mixture at a pressure of about 1,600 kPa to about 4,000 kPa.

30. The method or system according to any one of paragraphs 1 to 29, wherein the ethylene is separated from the second hydrocarbon mixture at a pressure of at least 400 kPa and less than 4,000 kPa.

31. The method or system according to any one of paragraphs 1 to 30, wherein the ethylene is separated from the second hydrocarbon mixture at a pressure of at least 600 kPa and less than 4,000 kPa.

32. The method or system according to any one of paragraphs 1 to 31, wherein the ethylene is separated from the second hydrocarbon mixture at a pressure of at least 800 kPa and less than 4,000 kPa.

33. The method or system according to any one of paragraphs 1 to 32, wherein the ethylene is separated from the second hydrocarbon mixture at a pressure of at least 1,000 kPa and less than 4,000 kPa.

34. The method or system according to any one of paragraphs 1 to 33, wherein the ethylene is separated from the second hydrocarbon mixture at a pressure of at least 1,400 kPa and less than 4,000 kPa.

35. The method or system according to any one of paragraphs 1 to 34, wherein the ethylene is separated from the second hydrocarbon mixture at a pressure of at least 1,600 kPa and less than 4,000 kPa.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments, other and further embodiments of the invention can be devised without departing from the basic scope thereof, and the scope thereof is determined by the claims that follow.

What is claimed is:

1. A method for separating one or more olefins comprising:
    separating at least a portion of $C_3$ and heavier hydrocarbons from a hydrocarbon comprising $C_1$ to $C_{20}$ hydrocarbons and hydroogen to provide a first hydrocarbon mixture comprising methane, ethane, ethylene, acetylene, and hydrogen;
    hydrogenating at least a portion of the first hydrocarbon mixture to convert at least a portion of the acetylene to ethane and ethylene to provide a hydrogenated mixture, wherein the hydrogenation is performed using contained hydrogen in the first hydrocarbon mixture, optionally supplemented by an external stream with hydrogen concentration of at least 50 mol %;
    cooling and condensing the hydrogenated mixture, at a temperature ranging from 5° C. to −40° C.;
    separating at least a portion of the methane from the condensed hydrogenated mixture to provide a second hydrocarbon mixture comprising ethane and ethylene; and
    separating at least a portion of the ethylene from the second hydrocarbon mixture to provide a first product comprising at least 97 mol % ethylene and a second product comprising at least 97 mol % ethane, wherein the at least a portion of ethylene is separated from the second hydrocarbon mixture using a vapor-liquid separator at a temperature greater than boiling point of propylene, that is greater than about −48° C. and at a pressure of about 360 kPa to about 4,000 kPa, wherein the hydrogenated mixture is cooled using refrigerated propylene.

2. The method of claim 1, further comprising transferring at least a portion of the second product to a pyrolysis furnace.

3. The method of claim 1, wherein the at least a portion of $C_3$ and heavier hydrocarbons are separated from the hydrocarbon comprising $C_1$ to $C_{20}$ hydrocarbons at a pressure of about 400 kPa to about 3,000 kPa.

4. The method of claim 1, wherein the at least a portion of methane is separated from the condensed hydrogenated mixture at a pressure of about 600 kPa to about 4,200 kPa, and the ethylene is separated from the second hydrocarbon mixture at a pressure of about 500 kPa to about 2,500 kPa.

5. The method of claim 1, wherein at least a portion of the hydrocarbon comprising $C_1$ to $C_{20}$ hydrocarbons is produced by cracking a heavy hydrocarbon containing $C_4$+ hydrocarbons in a fluid catalytic cracker, a pyrolytic process, or combination thereof.

6. The method of claim 1, wherein the at least a portion of $C_3$ and heavier hydrocarbons are separated from the hydrocarbon comprising $C_1$ to $C_{20}$ hydrocarbons at a pressure of about 800 kPa to about 2,000 kPa, the methane is separated from the condensed, hydrogenated mixture at a pressure of about 900 kPa to about 3,500 kPa, and the ethylene is separated from the second hydrocarbon mixture at a pressure of about 500 kPa to about 2,500 kPa.

7. The method of claim 1, wherein the at least a portion of the first hydrocarbon mixture is hydrogenated in the presence of a catalyst.

8. The method of claim 1, wherein a methane concentration in the hydrocarbon comprising $C_1$ to $C_{20}$ hydrocarbons is less than 12 mol %.

9. A method for separating one or more olefins comprising:

compressing a fluid comprising $C_1$-$C_{20}$ hydrocarbons, water, one or more acid gases, and hydrogen to obtain a compressed fluid;
scrubbing at least a portion of the compressed fluid to remove at least a portion of the one or more acid gases to provide a scrubbed fluid;
separating at least a portion of the water from the scrubbed fluid to provide a dehydrated fluid containing less than 0.5 mol % water, wherein the dehydrated fluid comprises the $C_1$-$C_{20}$ hydrocarbons and hydrogen;
separating at least a portion of $C_4$ and heavier hydrocarbons from the dehydrated fluid to provide a hydrocarbon comprising $C_1$-$C_3$ hydrocarbons and hydrogen;
separating at least a portion of $C_3$ hydrocarbons from the hydrocarbon comprising $C_1$-$C_3$ hydrocarbons to provide a first hydrocarbon mixture comprising ethane, ethylene, acetylene, methane, and hydrogen, where the hydrogen concentration in the first hydrocarbon mixture is from about 0.1 mol % to less than 15 mol %;
hydrogenating at least a portion of the first hydrocarbon mixture to convert at least a portion of the acetylene to ethane and ethylene to provide a hydrogenated mixture, wherein the hydrogenation is performed using contained hydrogen in the first hydrocarbon mixture, optionally supplemented by an external stream with hydrogen concentration of at least 50 mol %;
cooling and condensing the hydrogenated mixture, at a temperature ranging from 5° C. to −40° C.;
separating at least a portion of the methane from the condensed, hydrogenated mixture to provide a second hydrocarbon mixture comprising ethane and ethylene; and
separating at least a portion of the ethylene from the second hydrocarbon mixture to provide a first product comprising at least 97 mol % ethylene and a second product comprising at least 97 mol % ethane, wherein the at least a portion of ethylene is separated from the second hydrocarbon mixture using a vapor-liquid separator at a temperature greater than boiling point of propylene, that is greater than about −48° C. and at a pressure of about 360 kPa to about 4,000 kPa, wherein the hydrogenated mixture is cooled using refrigerated propylene.

10. The method of claim 9, further comprising transferring all or a portion of the second product to a pyrolysis furnace.

11. The method of claim 9, wherein the fluid has a methane concentration of less than 15 mol %.

12. The method of claim 9, wherein the fluid has a hydrogen concentration of less than 15 mol %.

13. The method of claim 9, wherein the at least a portion of $C_4$ and heavier hydrocarbons are separated from the dehydrated fluid at a pressure of about 500 kPa to about 3,500 kPa.

14. The method of claim 9, wherein the at least a portion of $C_3$ hydrocarbons are separated from the hydrocarbon comprising $C_1$-$C_3$ hydrocarbons at a pressure of about 400 kPa to about 3,000 kPa.

15. The method of claim 9, wherein at least a portion of the $C_1$-$C_{20}$ hydrocarbons is produced by cracking a heavy hydrocarbon containing $C_4$+ hydrocarbons in a fluid catalytic cracker, a pyrolytic process, or a combination thereof.

16. The method of claim 9, wherein the at least a portion of $C_4$ and heavier hydrocarbons are separated from the dehydrated fluid at a pressure of about 800 kPa to about 2,000 kPa, the at least a portion of methane is separated from the condensed, hydrogenated mixture at a pressure of about 900 kPa to about 3,500 kPa, and the at least a portion of ethylene is separated from the second hydrocarbon mixture at a pressure of about 500 kPa to about 2,500 kPa.

17. The method of claim 9, wherein the at least a portion of ethylene is separated from the second hydrocarbon mixture at a pressure of about 500 kPa to about 2,500 kPa.

18. The method of claim 1, wherein the hydrogenated mixture is cooled using a chilling system, wherein the chilling system includes a first cooler, a first vapor/liquid separator receiving the cooled hydrogenated mixture from the first cooler, and a second cooler receiving a gaseous hydrogenated mixture from the vapor/liquid separator.

19. The method of claim 18, wherein the first cooler provides a first cooled condensed portion of the hydrogenated mixture, wherein the second cooler includes at least one heat exchanger and a second vapor/liquid separator, and wherein the second vapor/liquid separator provides at least a tail gas and a second cooled condensed portion of the hydrogenated mixture.

* * * * *